United States Patent
Cao et al.

(10) Patent No.: US 10,432,857 B2
(45) Date of Patent: Oct. 1, 2019

(54) SYSTEMS, METHODS, AND APPARATUSES FOR OPTIMIZING FIELD OF VIEW

(71) Applicants: LIFE TECHNOLOGIES HOLDINGS PTE LIMITED, Carlsbad, CA (US); PIERCE BIOTECHNOLOGY, INC., Carlsbad, CA (US)

(72) Inventors: Yanpeng Cao, Singapore (SG); Suk Hong, Roscoe, IL (US); Tiong Han Toh, Singapore (SG); Steven Yeo, Singapore (SG); Benyong Shi, Singapore (SG); Kok Siong Teo, Singapore (SG); Brian Webb, Roscoe, IL (US)

(73) Assignees: LIFE TECHNOLOGIES HOLDINGS PTE LIMITED, Singapore (SG); PIERCE BIOTECHNOLOGY, INC., Rockford, IL (US)

( * ) Notice: Subject to any disclaimer, the term of this patent is extended or adjusted under 35 U.S.C. 154(b) by 161 days.

(21) Appl. No.: 15/782,996

(22) Filed: Oct. 13, 2017

(65) Prior Publication Data
US 2018/0124313 A1    May 3, 2018

Related U.S. Application Data

(60) Provisional application No. 62/408,013, filed on Oct. 13, 2016.

(51) Int. Cl.
| | |
|---|---|
| *H04N 5/232* | (2006.01) |
| *G02B 21/36* | (2006.01) |
| *G02B 27/02* | (2006.01) |
| *G06K 9/00* | (2006.01) |
| *G06T 7/30* | (2017.01) |

(Continued)

(52) U.S. Cl.
CPC ..... *H04N 5/23238* (2013.01); *G02B 17/0694* (2013.01); *G02B 21/365* (2013.01); *G02B 27/025* (2013.01); *G06K 9/00134* (2013.01); *G06T 7/30* (2017.01); *G06T 7/73* (2017.01); (Continued)

(58) Field of Classification Search
CPC ......... H04N 5/23238; G06T 7/30; G06T 7/73; G02B 17/0694; G02B 21/365; G02B 27/025; G02B 27/026; G06K 9/00134; G01N 27/44721
See application file for complete search history.

(56) References Cited

U.S. PATENT DOCUMENTS

| | | | |
|---|---|---|---|
| 4,845,558 A | 7/1989 | Tsai et al. | |
| 9,285,578 B2 * | 3/2016 | Staker | G02B 21/365 |

(Continued)

OTHER PUBLICATIONS

Anonymous: "BioDoc-It2 Imaging Systems Brochure".
(Continued)

*Primary Examiner* — Luong T Nguyen

(57) ABSTRACT

A method to maximize use of the field of view for an imaging system is provided herein. An imaging device can be part of the imaging system and include a detection unit and an alignment unit. The method includes capturing an initial image of an object and then calculating a rotational angle and zoom factor for the object in order to maximize the object's footprint within the field of view. Once the calculations are complete a computer can instruct the detection and alignment units to reconfigure their orientations relative to the object.

23 Claims, 20 Drawing Sheets

(51) Int. Cl.
*G06T 7/73* (2017.01)
*G02B 17/06* (2006.01)
*G01N 27/447* (2006.01)

(52) U.S. Cl.
CPC ... *H04N 5/23296* (2013.01); *G01N 27/44721* (2013.01); *G02B 27/026* (2013.01)

(56) References Cited

U.S. PATENT DOCUMENTS

| | | |
|---|---|---|
| 9,310,600 B2* | 4/2016 | Thrush ................. G02B 21/361 |
| 9,329,375 B2* | 5/2016 | Zuest ................. G02B 21/0016 |
| 2007/0064224 A1 | 3/2007 | Kreh et al. |
| 2007/0147673 A1* | 6/2007 | Crandall ............. G02B 21/367 |
| | | 382/128 |
| 2009/0128618 A1 | 5/2009 | Fahn et al. |
| 2012/0099852 A1 | 4/2012 | Staker et al. |
| 2014/0211031 A1* | 7/2014 | Han ................... H04N 5/23222 |
| | | 348/208.99 |
| 2014/0219540 A1* | 8/2014 | Drichel ................ G06K 9/3275 |
| | | 382/137 |

OTHER PUBLICATIONS

Anonymous: "Gel Doc (TM) XR+Instruction Manual", 2011.
Anonymous: "Getting Started Manual GeneSys", 2011 (2011).
"How to document the gel?", Youtube, May 20, 2012 (May 20, 2012), p. 1.
"Alphaimager HP. EP and EC User Guide", Jun. 2, 2010.

* cited by examiner

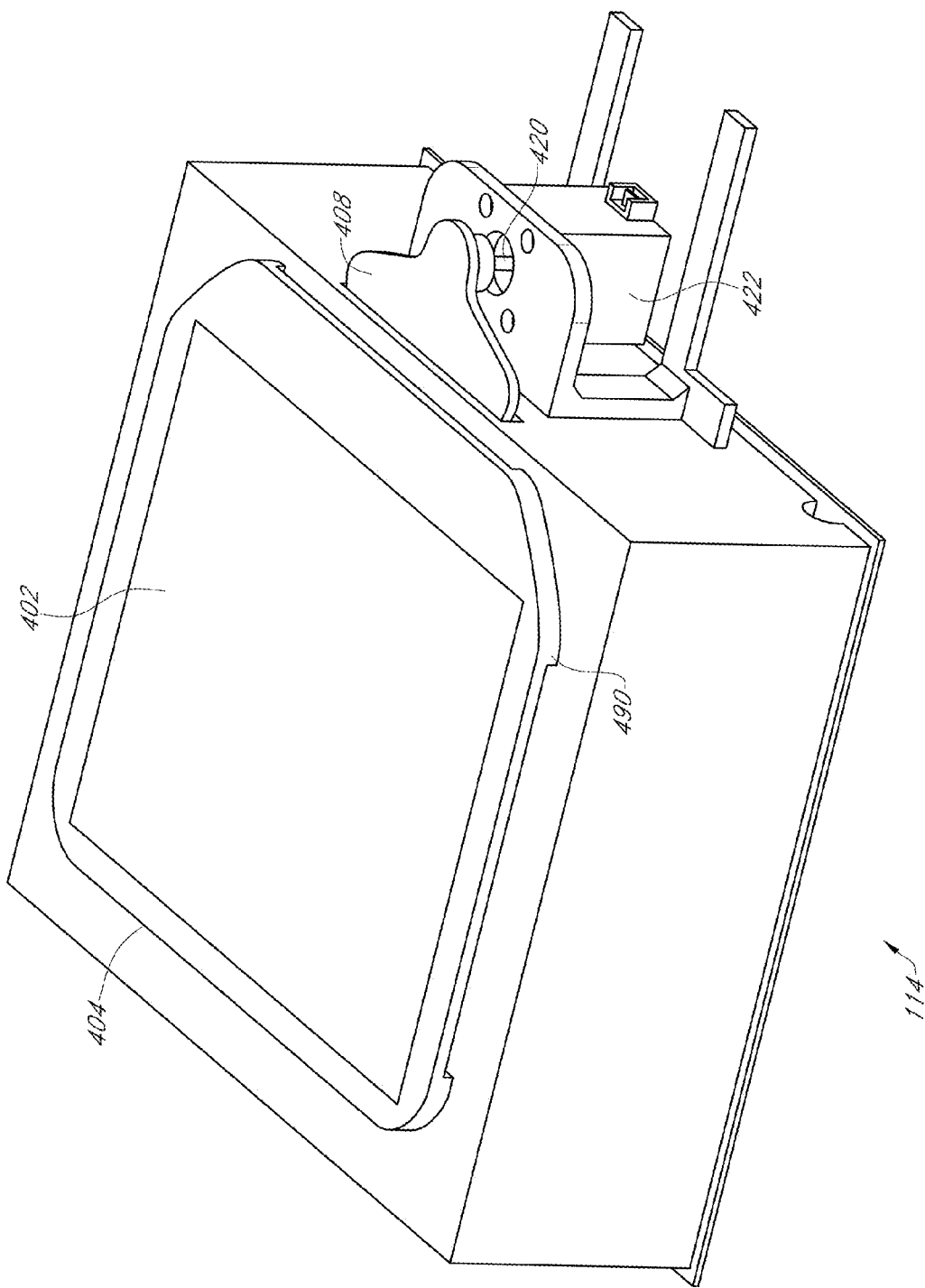

SYSTEMS, METHODS, AND APPARATUSES FOR OPTIMIZING FIELD OF VIEW

CROSS-REFERENCE TO RELATED APPLICATIONS

This application claims the benefit of priority of U.S. Provisional Patent Application No. 62/408,013 filed Oct. 13, 2016.

FIELD

The present disclosure generally relates to optical systems, methods, and apparatuses for maximizing the size of an object within a field of view. The systems, methods, and apparatuses disclosed herein apply to maximizing utilization of field of view by increasing the footprint of any object within a field of view. In particular, the present disclosure relates to systems, methods, and apparatuses for optimizing image capture by computing an optimized rotational geometry and zoom based on a first captured image in order to increase resolution and image quality of the object of interest.

BACKGROUND

The fields of biological imaging and imaging in general have benefited from improvements in digital camera technology as a whole. One such improvement has been an increase in the number of pixels detectors in modern cameras which has led to higher resolution images and, therefore, higher quality data generation.

Gel electrophoresis is a common procedure for the separation of biological molecules, such as DNA, RNA, polypeptides and proteins. In gel electrophoresis, molecules can be separated into bands according to the rate at which an imposed electric field causes them to migrate through a filtering gel. A gel enclosed in a glass tube or sandwiched as a slab between glass or plastic plates can be utilized. Gels have an open molecular network structure, defining pores that are saturated with an electrically conductive buffered solution of a salt. These pores are large enough to enable passage of the migrating macromolecules through the gel.

One problem with electrophoresis gels is that they are not always the same size or shape and they are often positioned in imaging devices with varying positions and orientations. Also, the bands are often irregular or imperfectly formed. Bands can appear curved, crooked, or sometimes faint. These problems are well known in the field and present analysis challenges.

Another problem with conventional gel imaging devices is that they fail to utilize their light sensors efficiently by imaging large portions of background which contains irrelevant information.

Therefore, there is a need in the art to create a system, method, and apparatus to image electrophoresis gels with varying attributes and to acquire the highest quality images possible to increase image resolution and therefore data precision and accuracy. Such a system will maximize the use of a detector's pixel sensors by increasing the footprint an object, or electrophoresis gel, consumes in the detector's field of view.

SUMMARY

Optical systems, methods and apparatuses are disclosed herein for maximizing field of view of an object with an image capturing device or system. In such systems, methods and apparatuses, an image of an object in a first position is captured within a field of view. A rotational angle to align an edge of the object with an edge of the field of view is then calculated, and a zoom factor to position the edge of the object along the edge of the field of view is also calculated.

In certain embodiments, the optical systems for maximizing field of view of an object with an image capturing device or system include a camera to capture the image of the object and a processor with instructions to calculate the rotational angle and the zoom factor. Embodiments may include a surface configured to rotate based on the calculated rotational angle and for the zoom of the image capturing device or system to be adjusted based on the calculated zoom factor. The adjusted zoom can be achieved mechanically in certain embodiments.

In certain embodiments, the image capturing device or system is configured to image the object in a second position within the field view. In certain embodiments, the second position may be optimized for the image of the object to be captured using a larger portion of the field of the view than the first image and for the second image of the object to be in an improved rotational alignment than the first image.

In certain embodiments, the optical system includes a display and a processor that is configured to create a virtual image to be presented on the display based on the calculated rotational angle and/or calculated zoom factor. The virtual image can be virtually rotated and/or virtually zoomed by an end user in certain embodiments.

In certain embodiments, the methods for maximizing field of view of an object with an image capturing device or system comprise capturing an image of an object in a first position within a field of view, calculating a rotational angle by virtually aligning an edge of the object with an edge of the field of view, calculating a zoom factor to position the edge of the object along the edge of the field of view, repositioning the object in a second position relative to the field of view based on the calculations, and then imaging the object in the second position to create a second image. The object in the second image may cover a larger portion of the field of view than the object covered in the first image.

In certain embodiments, the repositioning uses a moveable surface to reposition the object within the field of view. In certain embodiments, the repositioning uses a mechanical zoom to achieve the calculated zoom factor. In certain embodiments, the methods additionally include creating a virtual representation of a virtually zoomed and/or rotated image. The virtual images are configured to be manipulated by an end user in certain embodiments.

In certain embodiments, the methods for maximizing field of view of an object with an image capturing device or system comprise capturing an image of an object in a first position within a field of view, calculating a rotational angle by virtually aligning an edge of the object with an edge of the field of view, rotating the object relative to the field of view based on the calculated rotational angle, capturing an image of the object in a second position within the field of view, calculating a zoom factor to position the edge of the object along the edge of the field of view, increasing the size of the object within the field of view based on the zoom factor, and capturing an image of the object in a third position to create a third image. The second position may be optimized for the second image of the object to be captured in an improved rotational alignment than the first image in the first position. The third position may be optimized for the third image of the object to be captured using a larger portion of the field of the view than the first image in the first position.

In certain embodiments, the methods include creating a virtual image that can be manipulated by an end user. The virtual image may be configured to be rotated and/or zoomed by the end user. Embodiments may provide for rotating the object based on rotating a surface holding the object to achieve the calculated rotational angle. Embodiments may also provide for mechanical zoom adjustment to achieve the calculated zoom factor.

BRIEF DESCRIPTION OF THE SEVERAL VIEWS OF THE DRAWINGS

For a more complete understanding of the principles disclosed herein, and the advantages thereof, reference is now made to the following descriptions taken in conjunction with the accompanying drawings, in which:

FIG. 4B is an illustration of an alignment unit including a motor and drive shaft according to one of the various embodiments.

Figure 1:
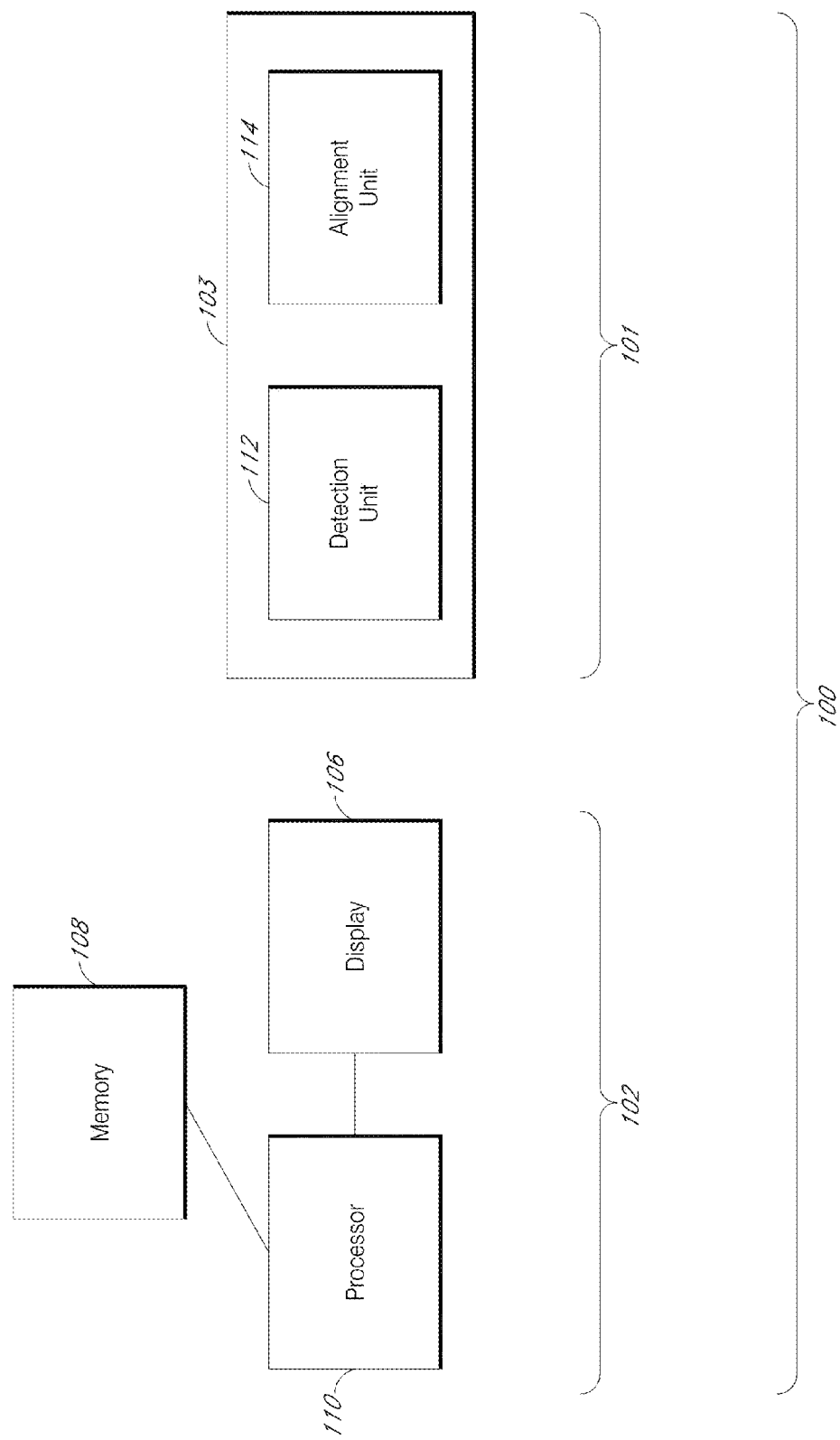
FIG. 1 is an illustration of an imaging system according to one of the various embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In order that the present disclosure may be more readily understood, certain terms are first defined. Additional definitions are set forth throughout the detailed description.

DETAILED DESCRIPTION OF THE EMBODIMENTS

Embodiments of systems, methods, and apparatuses for imaging systems are described in the accompanying description and figures. In the figures, numerous specific details are set forth to provide a thorough understanding of certain embodiments. A skilled artisan will be able to appreciate that the imaging systems, methods, and apparatuses described herein can be used in a variety of instruments using optical trains including, but not limited to, electrophoresis gel imaging devices. Additionally, the skilled artisan will appreciate that certain embodiments may be practiced without these specific details. Furthermore, one skilled in the art can readily appreciate that the specific sequences in which methods are presented and performed are illustrative and it is contemplated that the sequences can be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In order that the present disclosure may be more readily understood, certain terms are first defined. Additional definitions are set forth throughout the detailed description.

As used herein "about" means plus or minus 20%, more preferably plus or minus 10%, even more preferably plus or minus 5%, most preferably plus or minus 2%.

As used herein "field of view" means the area that is visible to a camera or detection device.

As used herein "pixel sensors" refers to anything that can convert light into a digitally encoded signal. Pixel sensors can refer to an integrated circuit containing an array of pixel sensors with each pixel sensor containing a photodetector and an active amplifier.

As used herein "edge" means the outside limit of an object, area, or surface.

As used herein "border" means the edge or boundary of something.

In various embodiments, the imaging system and method disclosed in the present application can be used in conjunction with various apparatuses, systems, and methods relating to electrophoresis gel imaging or imaging of any kind.

In gel imaging, instruments that are standard in the field generally consist of a housing, a platform to place a gel, an ultraviolet light to illuminate labels contained within the gel, and some kind of detection device such as a camera. The user generally manually positions a gel on the platform and then instructions a computer to activate the camera and capture an image. Once the image is transferred to the computer, the user can electronically manipulate the image using photo editing software available on the market (e.g. Photoshop). However, the skilled artisan will appreciate the difficulty in manually capturing the highest quality image possible. One such way to increase image quality is to utilize as many pixel sensors within a detection device as possible, thereby, increasing the resolution of the image.

Referring to FIG. 1, a schematic of an imaging system 100 in the field of electrophoresis gel imaging is shown according to an embodiment. The imaging device 101 may include a detection unit 112 configured to image objects in an alignment unit 114. In various embodiments, the alignment unit 114 may be configured to move an object's relative position to the detection unit 112. In various embodiments, the detection unit 112 may be configured to move relative to the position of an object within the alignment unit 114. A housing 103 may be configured to house the detection unit 112 and alignment unit 114. The housing 103 may be configured to house both the imaging device 101 and the computing device 102 (not shown). An object in the alignment unit 114 may be imaged by the detection unit 112 and that image can be transferred to a computing device 102 where image processing may occur. The computing device 102 may act to control the various components of the imaging device 101 or may interact with a separate controller to control the various components of the imaging device. In various embodiments, the hardware components are in electronic communication with the computing device 102 either through a wireless adaptor or a physical connection (e.g. USB, ethernet, etc.).

In various embodiments, the computing device 102 may include a memory 108, a processor 110, and a display 106 and may be configured to control the imaging device 101. The computing device 102 or controller may be any computer system known in the art, including a laptop computer, a desktop computer, and a workstation, and may in particular be any system including a bus, processor 110 coupled with the bus for processing information, and a memory 108 (e.g., RAM, ROM) or other dynamic storage device for storing information and/or instructions to be executed by the processor. Additionally, the memory 108 may store executable instructions to carry out any of the methods contained herein.

Figure 2:
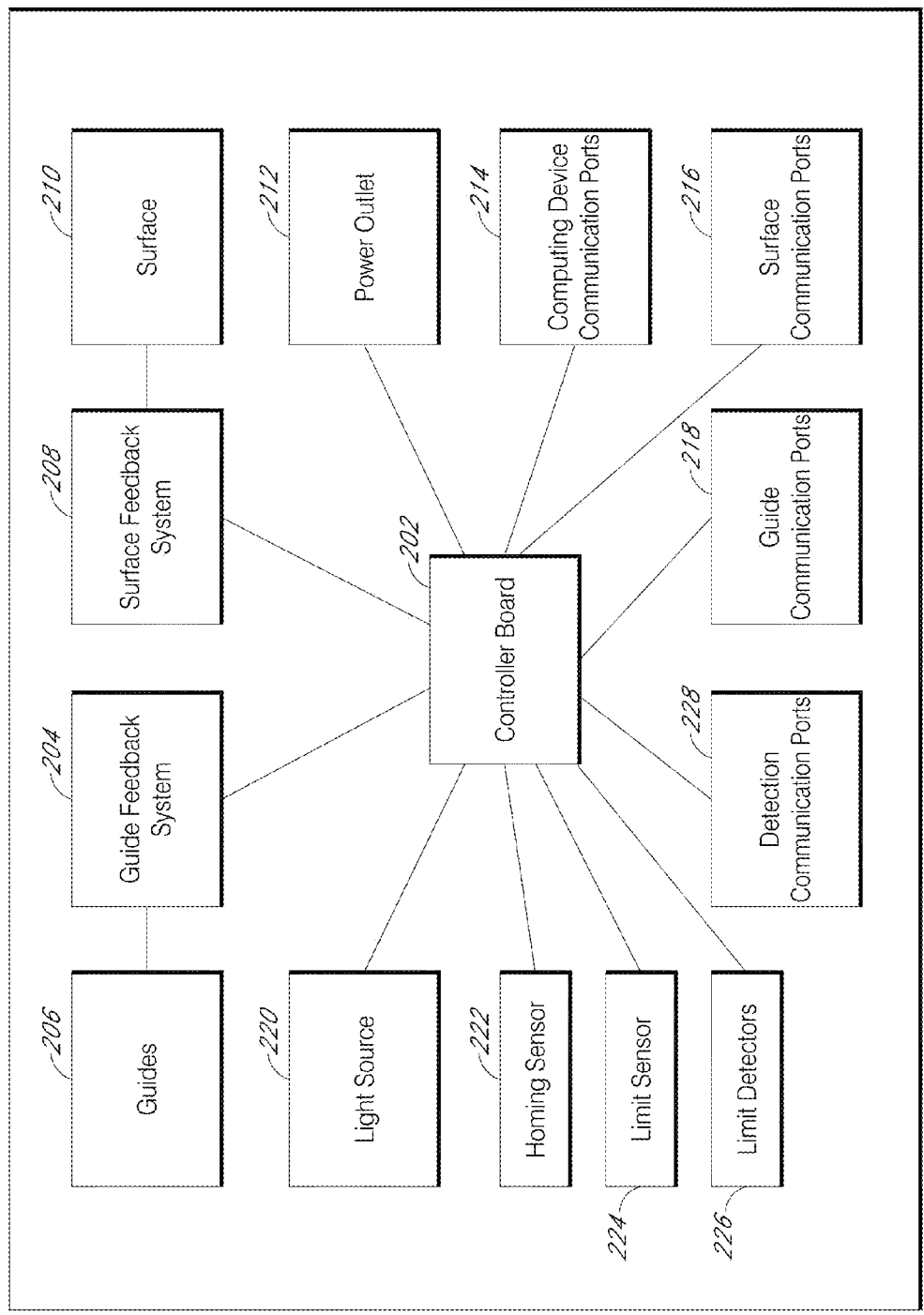
FIG. 2 is a schematic of an imaging device according to one of the various embodiments.

Referring to FIG. 2, a schematic of an imaging device 101 is shown according to an embodiment. The imaging device 101 may include a housing 103 configured to house a controller board 202 in communication with one or more other components, which may include one or more feedback systems including guide feedback systems 204 and surface feedback systems 208, at least one power outlet 212, computing device communication ports 214, surface communication ports 216, guide communication ports 218, detection communication ports 228, at least one light source 220, and various sensors and detectors, including, a homing sensor 222, limit sensor 224, and limit detectors 226. In various embodiments, the several components may be in electronic communication as indicated by the line connectors as shown in FIG. 2. In various embodiments, the guide feedback system 204 provides positional information from the guides 206 to the controller board. In various embodiments, the surface feedback system 208 provides positional information from the surface 210 to the controller board 202. The various feedback systems may be in electronic communication with the various sensors.

Figure 3A:
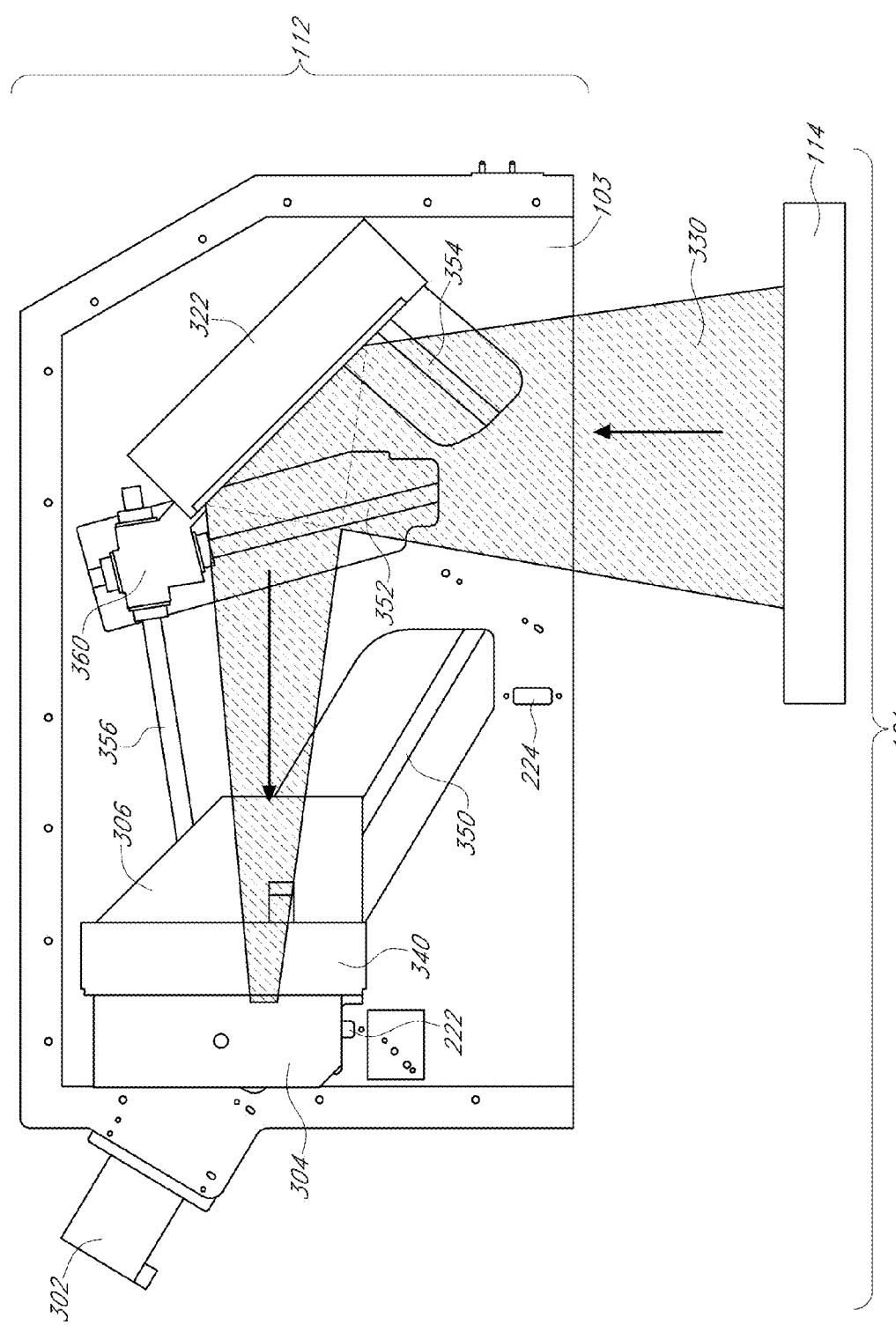
FIG. 3A is an illustration of a set of guides for coordinating the various elements of a detection unit in a long light path configuration according to one of the various embodiments.
Figure 3B:
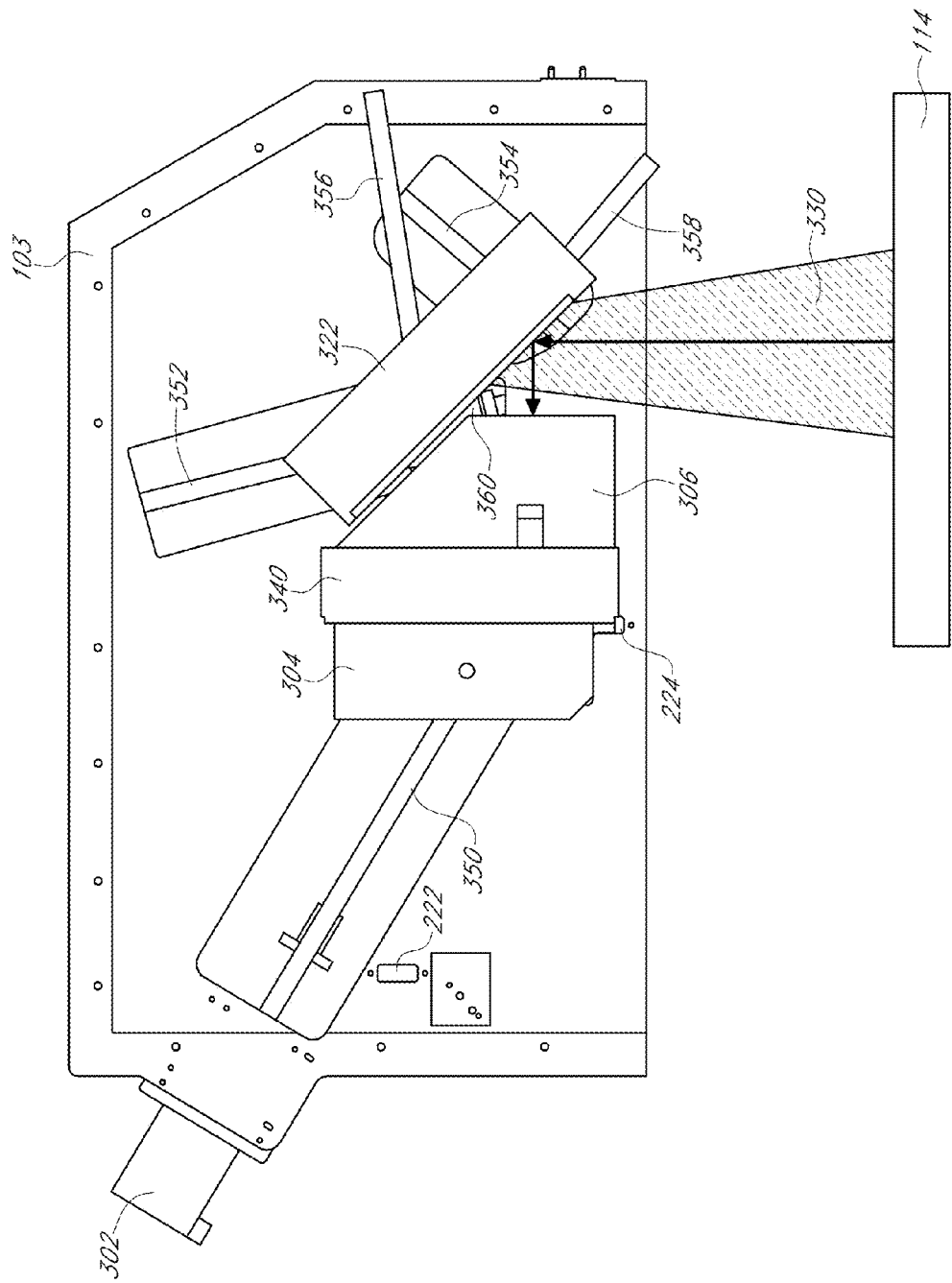
FIG. 3B is an illustration of a set of guides for coordinating the various elements of a detection unit in a short light path configuration according to one of the various embodiments.
Figure 3C:
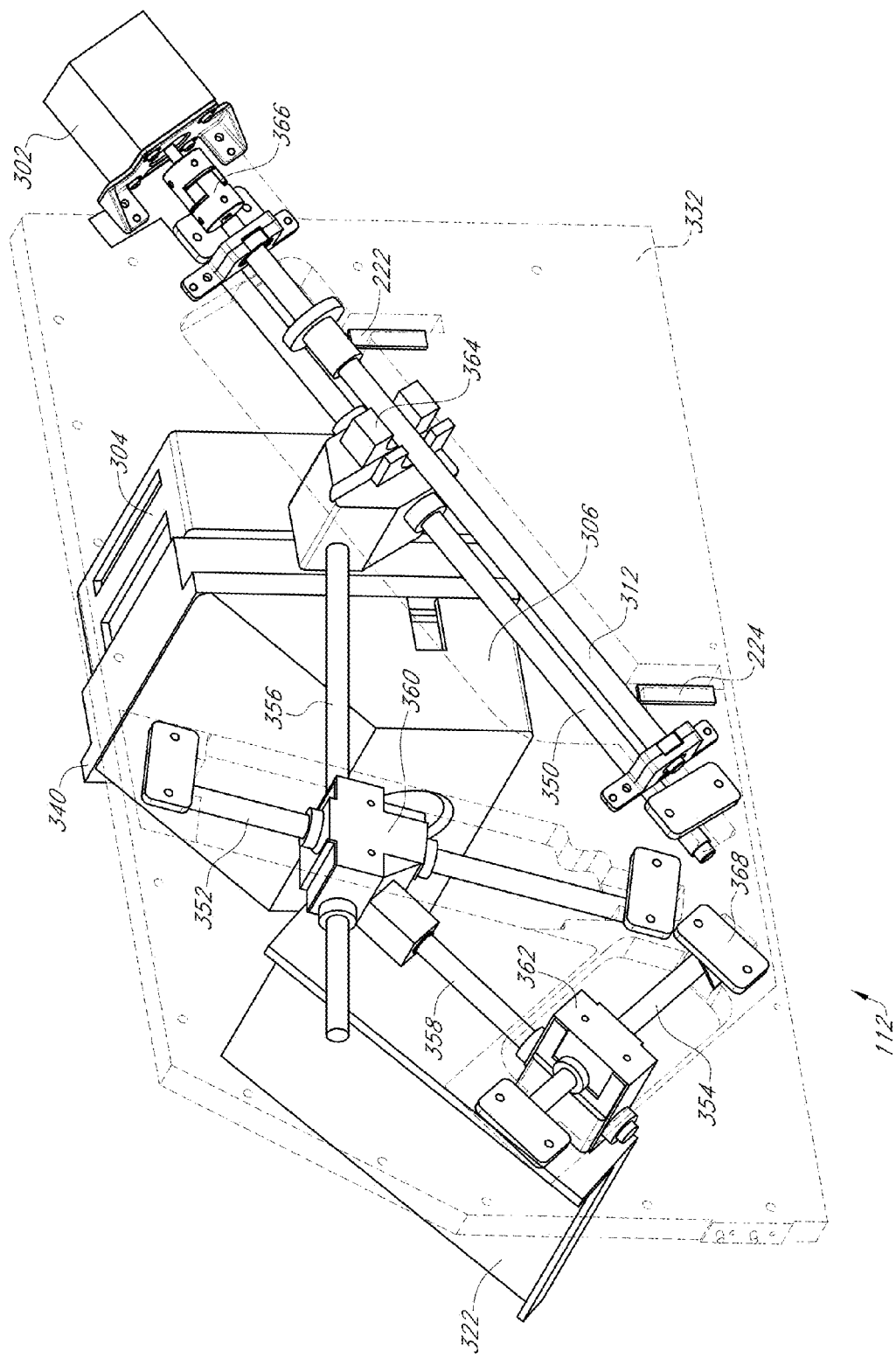
FIG. 3C is an illustration of the cross section view through the housing of an imaging device including a detection unit according to one of the various embodiments.

According to various embodiments described herein, any of the imaging devices 101 may include a detection unit 112. FIGS. 3A-3C illustrate various embodiments of a detection unit.

Referring to FIGS. 3A-3C the imaging device may include an alignment unit 114 and a detection unit 112 which may both be mounted within a housing 103 using techniques known in the art according to various embodiments. The detection unit 112, according to various embodiments, may include at least one motor 302 configured to drive several optical components along various guides. In various embodiments, the components include at least one camera 304, at least one emission filter 340, at least one optics 306, and at least one folding mirror 322. As depicted, the various components work to produce a light path 330 between the alignment unit and the camera 304. The camera 304 may send and receive instructions and data with the detection communication ports 228.

In various embodiments, a motor 302 may couple to a lead screw 312 with a coupler 366. The coupler 366 may serve to connect the lead screw 312 to the motor 302. The lead screw may 312 interact with threads on the camera block 364 or on a nut associated with the camera block 364 to drive movement of the camera block 364 along a detector guide 350. As the camera block 364 moves it may either push or pull a first power transmission shaft 356, thereby, transferring power through a transmission block 360 along a transmission guide 352. The transmission block 360 may slide/mount, through known techniques in the art, to a second power transmission shaft 358 and serve to transfer motion to a mirror block 362 which may drive a folding mirror 322 along a mirror guide 354. The motor may be controlled by the controller board 202 through one or more guide communication ports 218. The controller board 202 may receive positional information from one or more sensors used to detect the position of the various components along the various guides. The various sensors used to detect position can include infrared, reed switch, hall effect, laser distances, encoders, and anything else known or useful in the art. In various embodiments, a homing sensor 222 may be used to detect when the camera block 364 is in the "home" position or in the location where the light path 330 is longest. In other embodiments, the home position can be anywhere along the various guides. In various embodiments, a limit sensor 224 may detect when the camera block 364 is positioned such that the light path 330 is shortest and without light path 330 obstruction by components contained within the housing. In various embodiments, the several sensors may be configured to determine the position of the various blocks on the various guides 206 and send positional information to the controller board 202 through a guide feedback system 204. Once the controller board 202 receives positional information it can provide instructions to the motor 302 to actuate movement of the various components in the detection unit 112. In various embodiments, the guides and blocks are configured such that a light path 330 will always be directed from the alignment unit 114 to the camera 304. In various embodiments, the mirror guide 354, transmission guide 352, and detector guides 350 may be mounted to the housing 103 through a plate coupler 368. The plate coupler 368 may include screws, plates, welds, pins, or any other attachment means known in the art to affix the various guides to the housing 103.

In various embodiments, the camera block 364 slides along the detector guide 350 and interacts with the transmission shaft 356. In some embodiments, the interaction between the detector guide 350 and the transmission shaft 356 is through a screw, pin, clip, or anything known or useful in the art.

In various embodiments, the transmission block 360 can slide along the transmission guide 352 and interact with the transmission shaft 356. In some embodiments, the interaction between the transmission guide 352 and the transmission shaft 356 is through a screw, pin, clip, or anything known or useful in the art.

In various embodiments, the mirror block can slide along both the second power transmission shaft 358 and the mirror guide 354 at the same time.

In various embodiments, the light path 330 passes from the alignment unit 114 and to a folding mirror 322 that may be configured to bend the light path 330, thereby, positioning the light path 330 to pass through optics 306, the emission filter 340, and into the camera 304. The camera may include pixel sensors to convert a light signal to a digital signal. The digital information can be communicated to the controller board 202 or computer device 102 through electronic means known in the art (e.g. Network cable, USB, ethernet, etc.). In various embodiments, the emission filter 340 may include multiple emission filters that can be selected based on their transmissive properties.

In various embodiments, the detection unit 112 may include any commercially available camera 304 configured for optical and/or digital zoom without a system for mechanical zoom requiring a folded light path 330. In various embodiments, the camera can be configured to be repositioned in along x, y, z, axes or rotated or tilted to move in order to reposition a field of view relative to an object.

According to various embodiments described herein, any of the imaging devices 101 may include an alignment unit 114. FIGS. 4A-4F illustrate various embodiments of an alignment unit.

Referring to FIGS. 4A-4F an alignment unit 114 may include a surface 402 configured to support an object, a surface housing 404 configured to house the surface 402, a platform 410 configured to support the surface housing 404, a transilluminator box 412 positioned between the platform 410 and attached to a housing 103 through a connector 414 according an embodiment. In various embodiments, the surface is configured to change position using a motor 422 with a drive shaft 420 that is connected to the surface housing 404 through a drive linkage 408. In various embodiments, the drive linkage 408 connects to a surface housing 404 using a drive pin 406 and the drive pin 406 may fit into a groove 460 located on the platform. In various embodiments, the surface housing 404 can be supported by one or more support pins 430 positioned on the platform 410. In various embodiments, a boundary 440 on the platform 410 may interact with one or more protrusions 490 from the surface housing 404 to ensure that the surface moves along a known path. In various embodiments, one or more limit detectors 450 may be positioned on the platform to sense the position of the surface housing 404.

In various embodiments, the motor 422 engages a linkage 408 that is configured to interact with a surface housing 404 through a drive pin 406. According to various embodiments, FIGS. 4D and 4E describe the mechanics of rotation in an alignment unit 114. In FIG. 4D the motor 422 has turned a driveshaft 420 clockwise, thereby, turning the drive linkage 408 and drive pin 406 as well toward the clockwise direction. In various embodiments, a groove 460 in the surface housing 404 may serve as a track or guide for the drive pin 406. A curvature of the groove 460 may be included allowing the surface housing 404 to rotate in the opposite direction as the drive linkage 408. FIG. 4E describes the mechanics of surface 402 in the opposite direction. In various embodiments, the groove 460 position or orientation may be configured to drive the surface housing 404 along whatever path of motion is desirable.

Figure 4A:
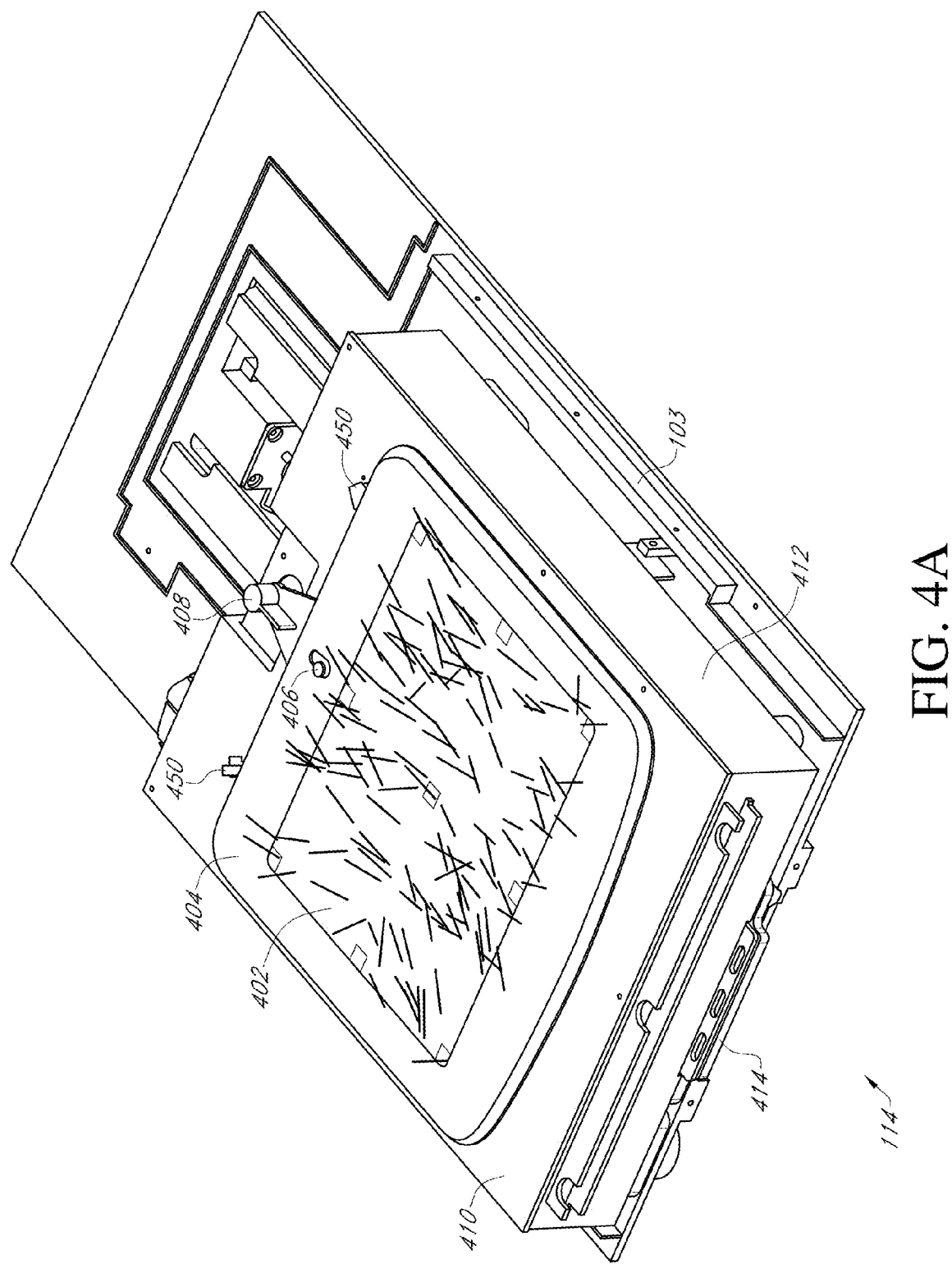
FIG. 4A is an illustration of an alignment unit according to one of the various embodiments.
Figure 4C:
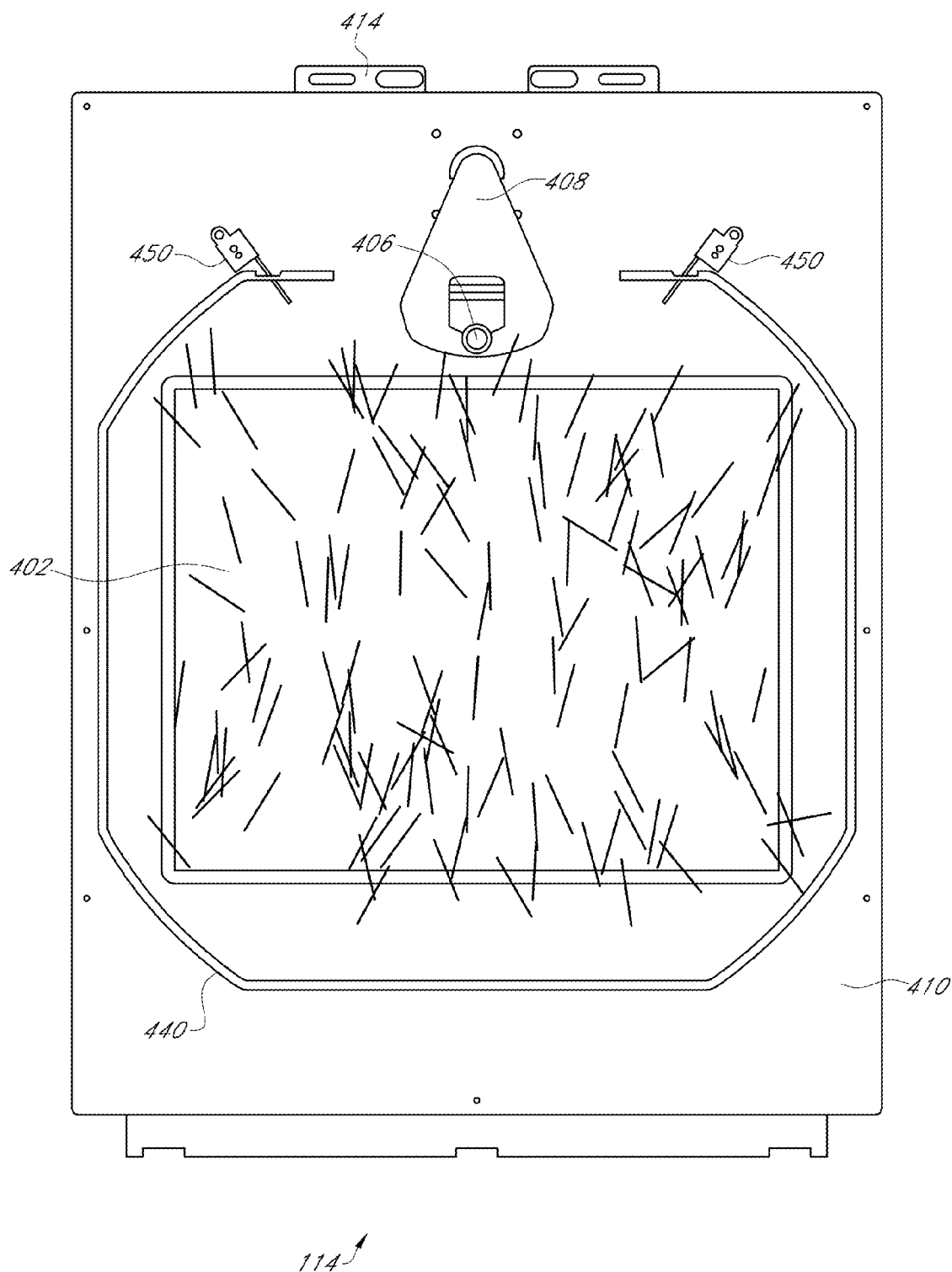
FIG. 4C is an illustration of an alignment unit with the surface housing removed according to one of the various embodiments.
Figure 4D:
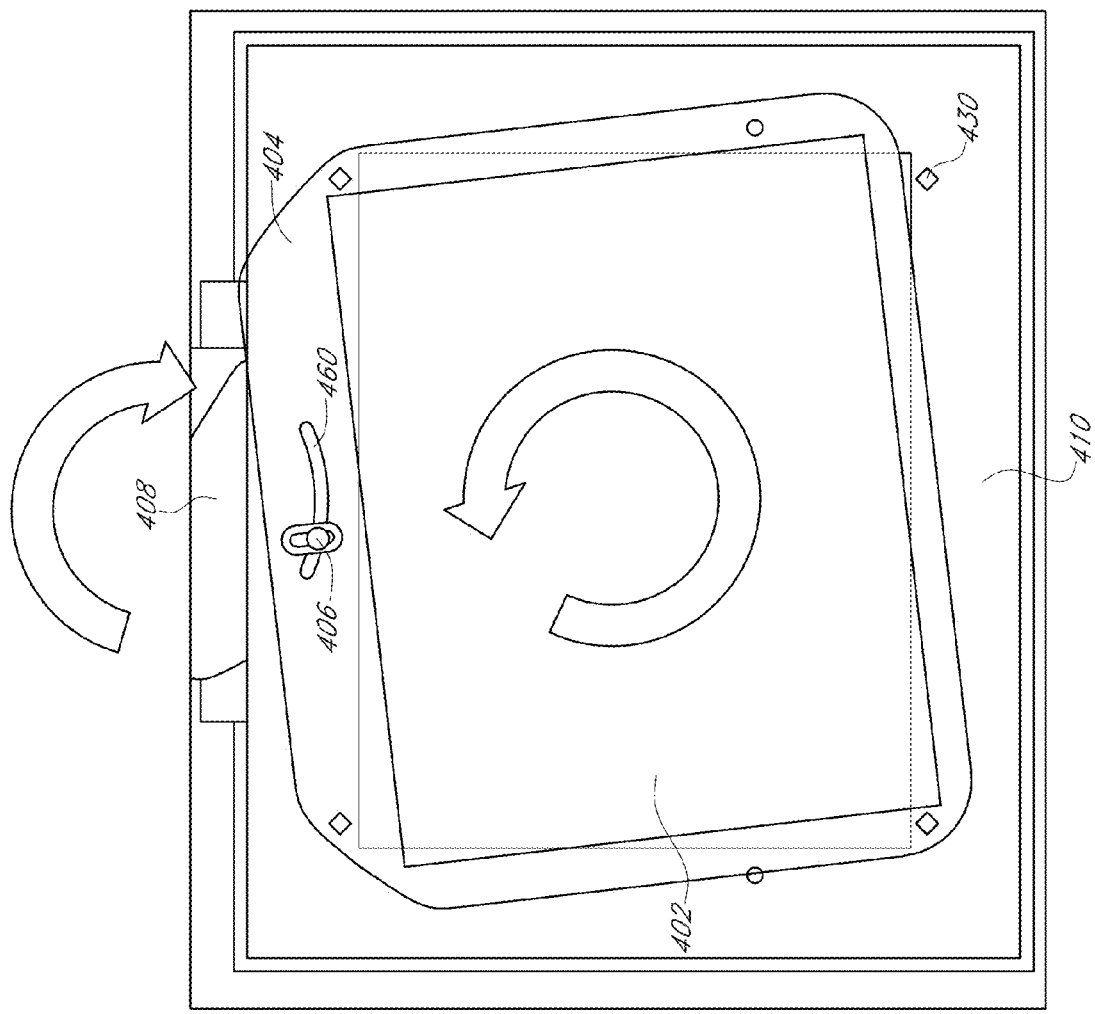
FIG. 4D is an illustration of an alignment unit with a rotated surface according to one of the various embodiments.
Figure 4E:
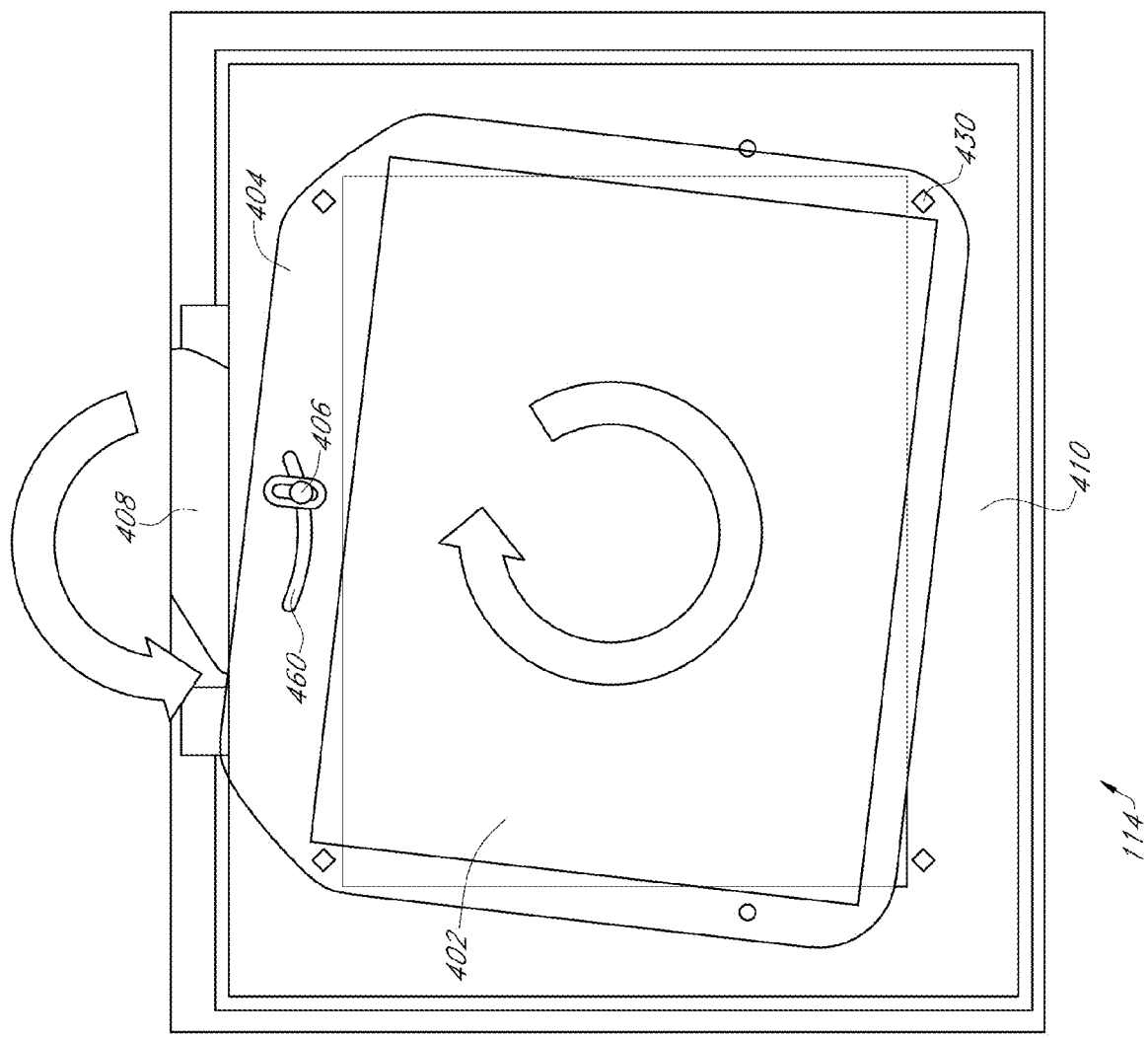
FIG. 4E is an illustration of an alignment unit with a rotated surface according to one of the various embodiments.

In various embodiments, one or more limit detectors, shown in FIGS. 4A and 4C, may be configured to detect the presence of a surface housing 404 and communicate its position to a controller board 202 via a surface feedback system 208. The controller board 202 may send instructions to the motor 422 to make position adjustments through a surface communication port 216.

Figure 4F:
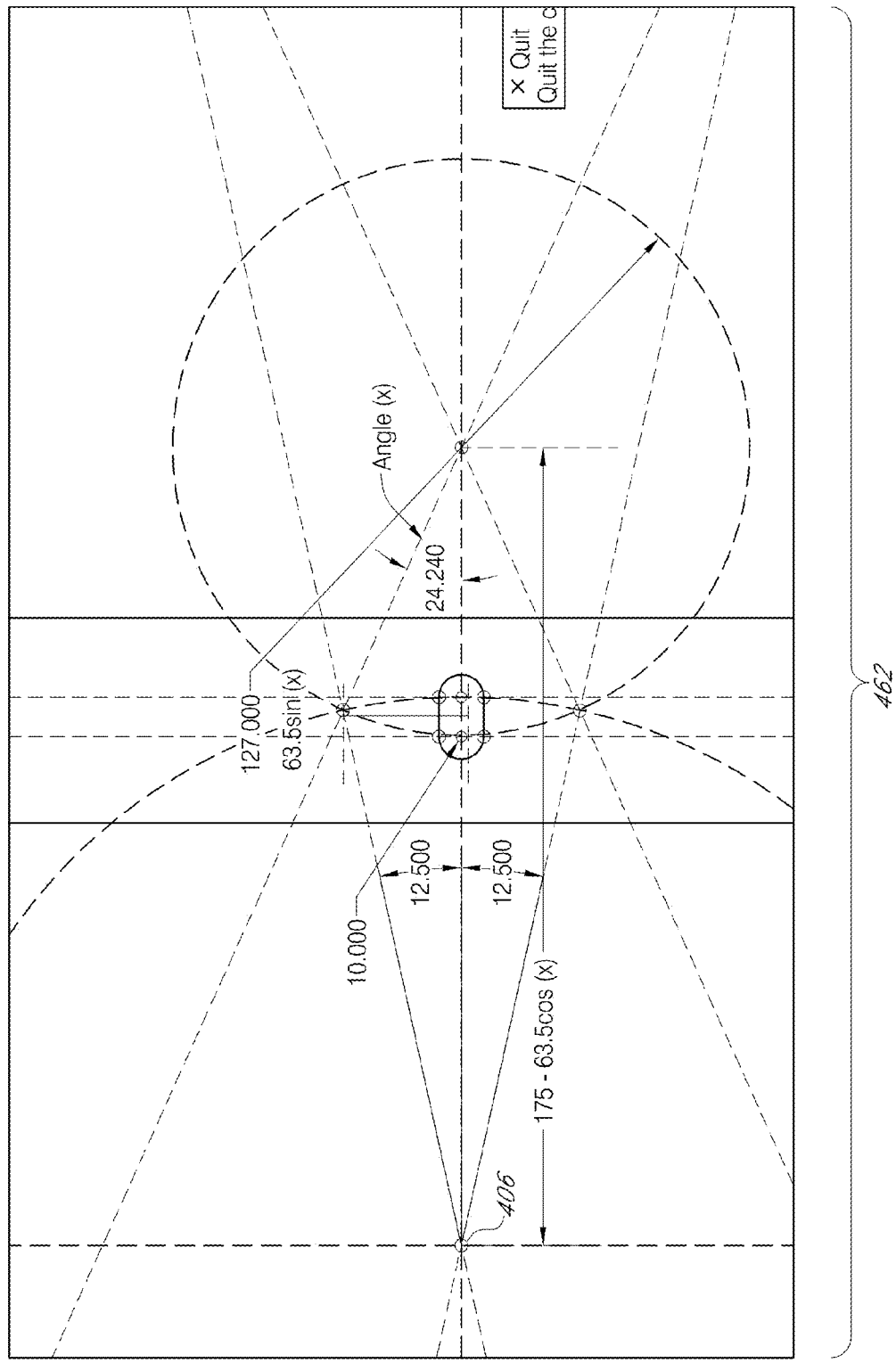
FIG. 4F is a graphical representation of rotational alignment geometry of the alignment unit according to one of the various embodiments.

Referring to FIG. 4F a surface rotation geometry 462 is shown according to an embodiment. In various embodiments of an alignment unit 114, the surface 402 may be rotated 12.5 degrees in either direction. In various embodiments, left center circle.

In various embodiments, the alignment unit 114 may include any moveable platform capable of supporting an electrophoresis gel. Such an alignment unit 114 may move in the x, y, z, or rotational directions.

Figure 5:
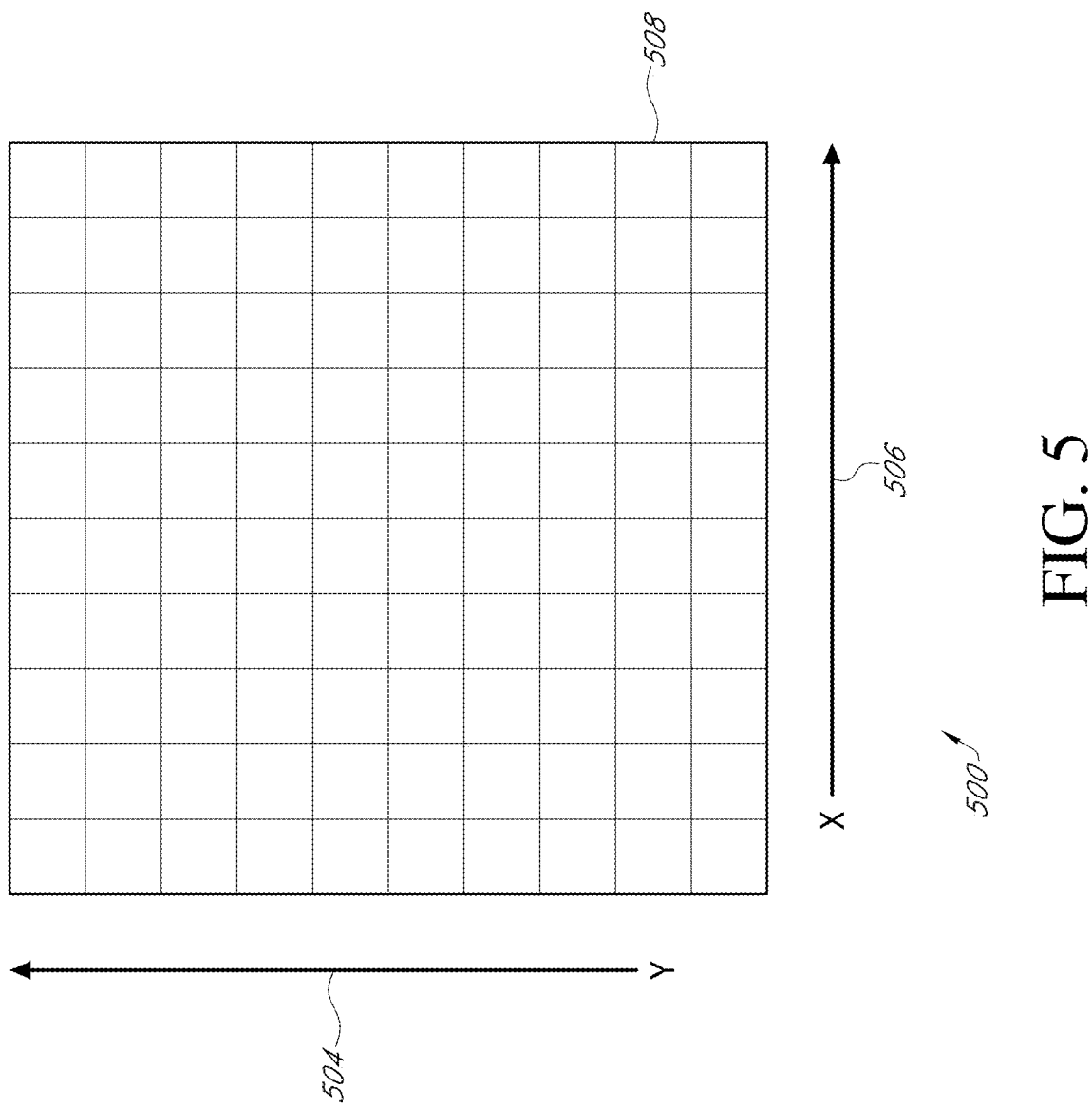
FIG. 5 is an illustration of a field of view for a camera with an overlapping grid indicating the location of pixel sensors according to one of the various embodiments.

FIG. 5 illustrates a field of view 500 according to one embodiment. Every detection device or camera 304 has a field of view 500 and in modern photography light coming into a field of view is picked up by an array of pixel sensors 508. In FIG. 5, each pixel sensor 508 has been given a coordinate on an x and y axis 504, 506. In part, the resolution of an object within a field of view is determined by the amount of space that object covers in the field of view 500. For this reason, photographers usually try to approach a subject or use optical zooming in order to maximize the number of pixel sensors uses, thereby, increasing the resolution and quality of an image.

Figure 6A:
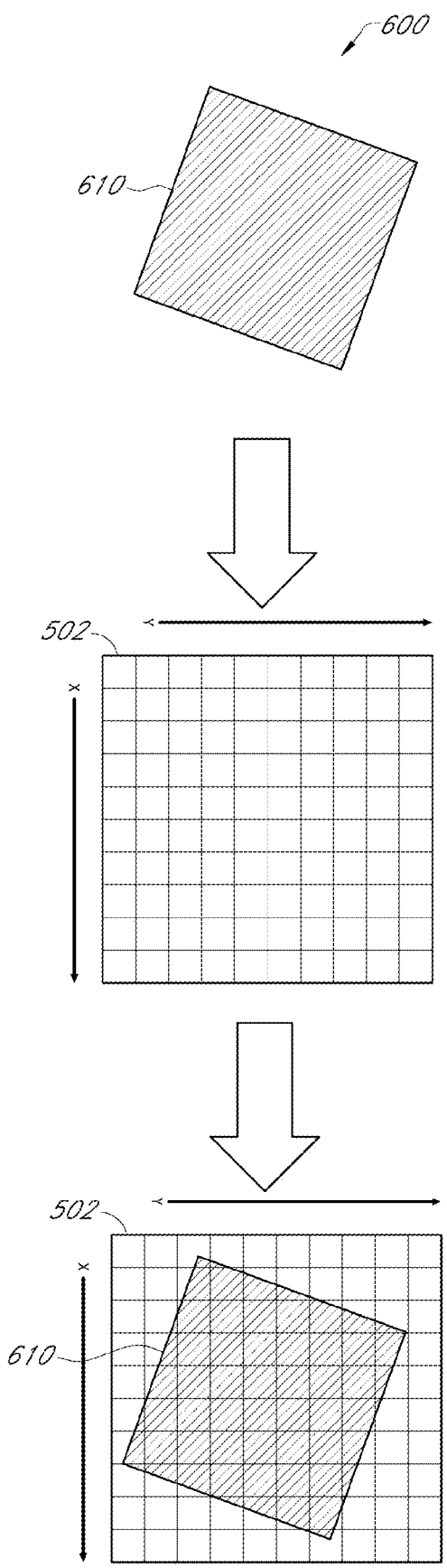
FIGS. 6A-6B are flow diagrams of an image capture method according to the prior art.
Figure 6B:
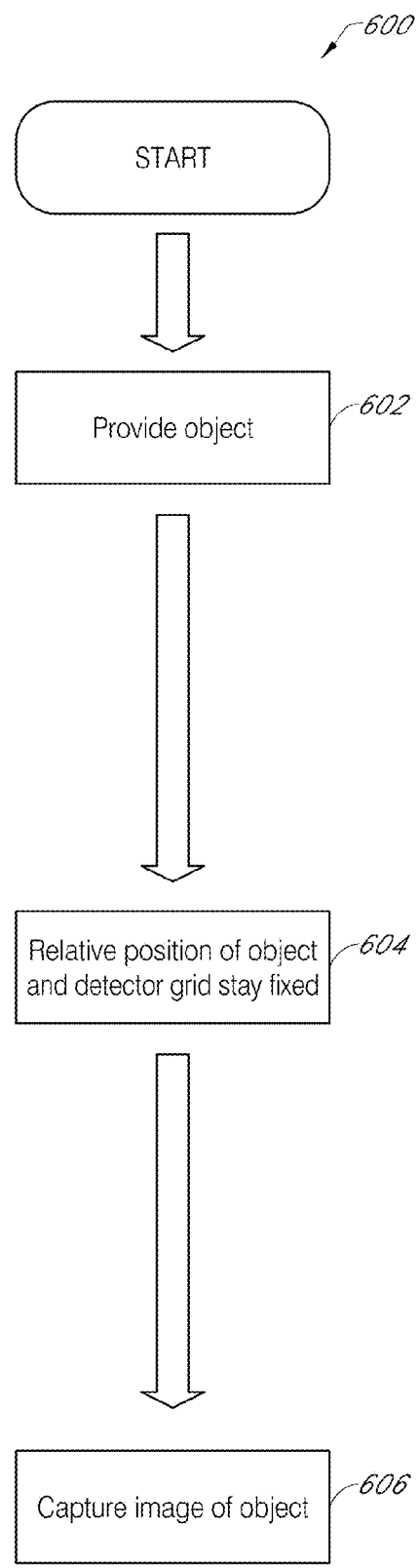

FIGS. 6A and 6B illustrate a prior art method of image capture, and more specifically, a method of electrophoresis gel imaging. In step 602, an object 610 is provided (e.g. electrophoresis gel). In step 604, the relative position of the object 610 and detector grid 502 stays fixed. In step 606, an image of the object 610 is captured. The problem with such a method is that many pixel sensors 508 remain unused because the field of view 500 covers much more area than that covered by the object which lowers the quality of the imaged object. A solution would be to rotate the object's relative position such the edges of the object 610 and detector grid 502 are aligned and then zoom in mechanically or optically to maximize the number of pixel sensors detecting signal coming from the object 610.

Figure 7A:
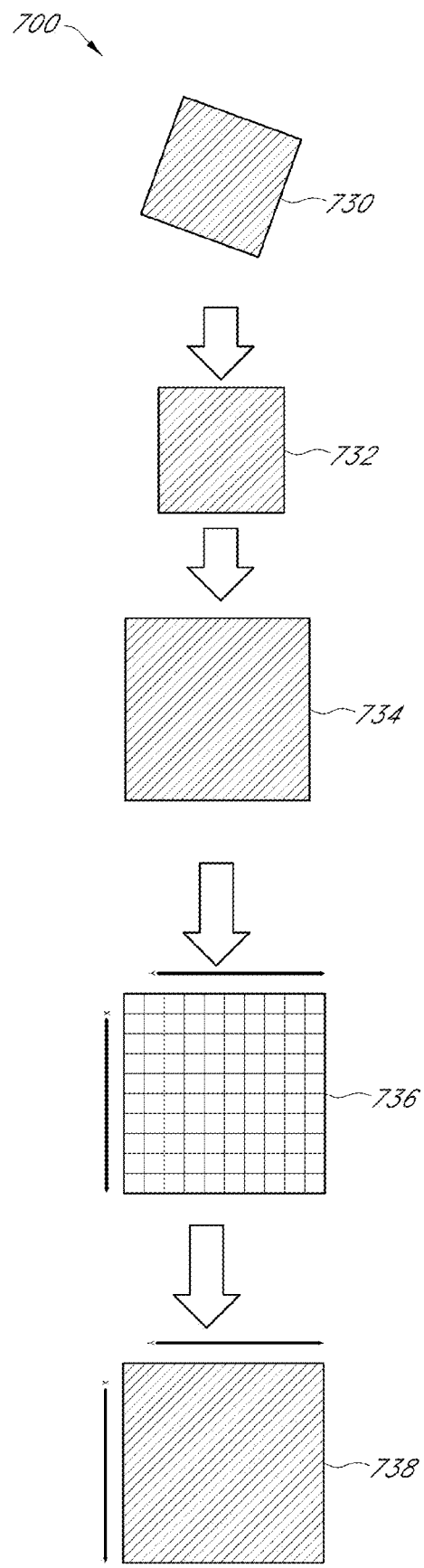
FIGS. 7A-B are flow diagrams of an image capture method according to one of the various embodiments.
Figure 7B:
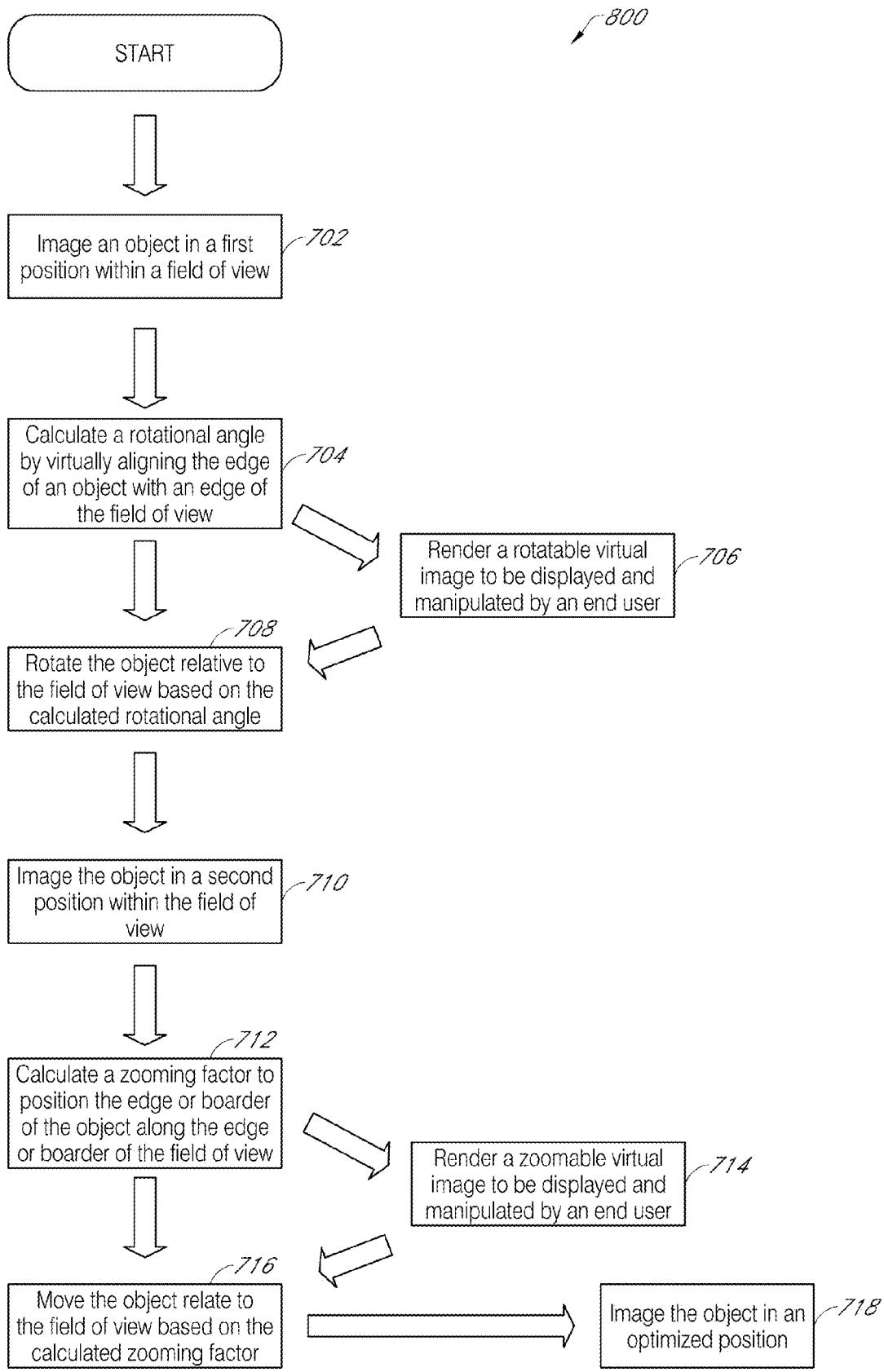

FIGS. 7A and 7B illustrate an optimized image capture method 700, according to an embodiment, which may be carried about by the imaging system 100 described herein. In step 702, an object 730 may be imaged in a first position within the field of view 500 to generate a first image. In step 704, a rotational angle may be calculated by virtually aligning the edge of an object 730 with the edge of the field of view 500. In optional step 706, a rotatable virtual image may be displayed and manipulated by an end user. In step 708, the object 730 may be rotated relative to the field of view 500 based on the calculated rotational angle. In step 710, the object 730 may be imaged within the field of view 500 in a second position to generate a second image. In step 712, a zoom factor may be calculated to position the edge or border of the object 730 along the edge or border of the field of view 500. In optional step 714, a zoomable virtual image may be displayed and manipulated by an end user. In step 716, the object 730 may be moved relative to the field of view based on the calculated zoom factor. In step 718, the object 730 may be imaged in an optimized position to generate a third image.

Referring to FIG. 7A, the method presented above 700 is shown graphically. According to one embodiment, the object 730 starts in a rotated and unzoomed position which, in conventional imaging methods the final image, would be captured. According to an embodiment the object 730 is rotated to become a rotated object 732 and later zoom is implemented so that the object becomes a zoomed object 734. The object 730 that has been rotated and zoomed relative to the field of view 500 utilizes more pixel sensors 736 than in the prior art, thereby, producing higher quality images capable of producing higher quality data.

Figure 8A:
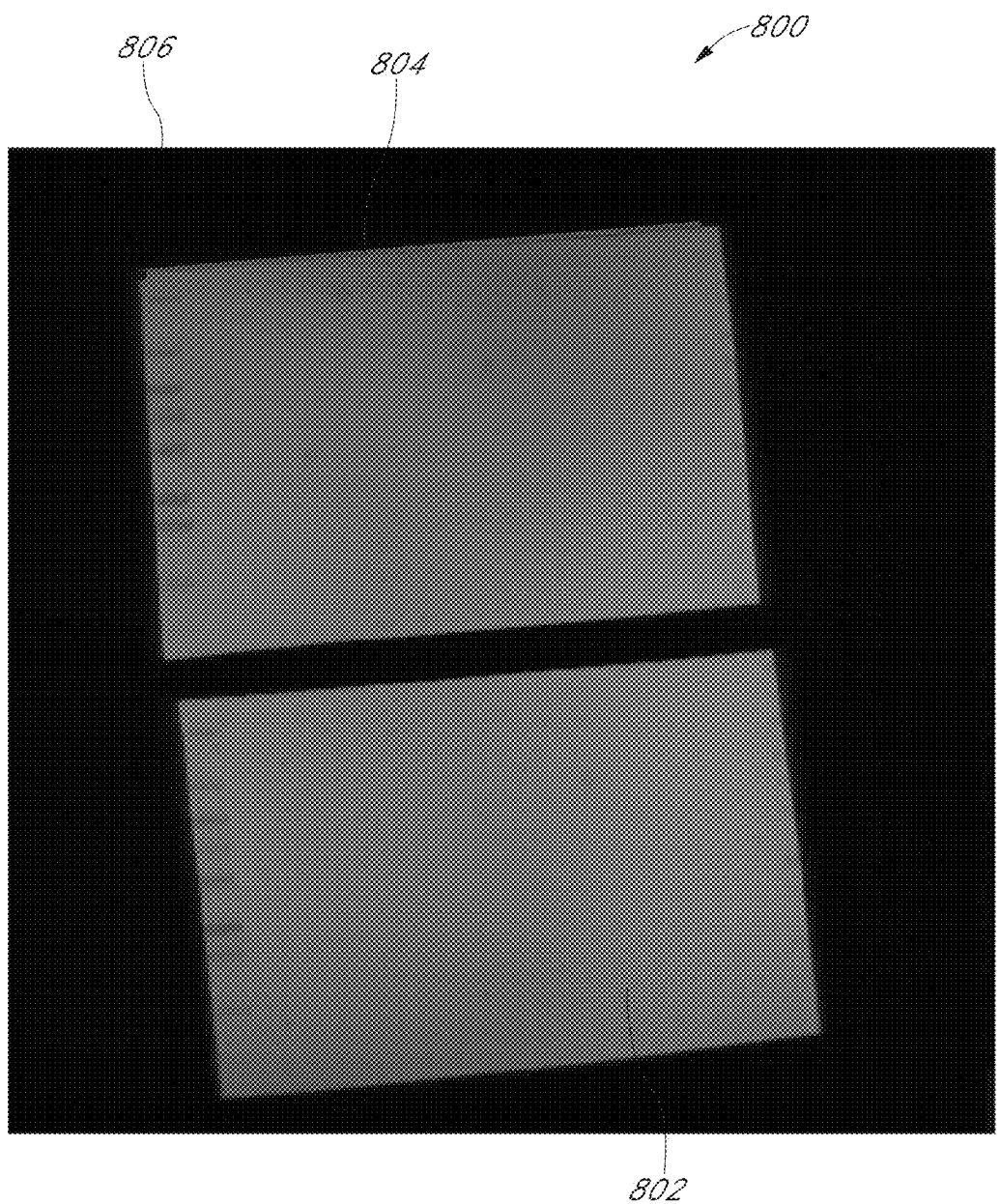
FIG. 8A is an illustration of an electrophoresis gel in a non-optimized field of view.

Referring to FIG. 8A, a photograph of an object 802 that was positioned within an alignment unit 114 (see FIG. 4) was captured within the field of view 500 of a detection unit 112 (See FIG. 3) before any automation has occurred. The image 800 shown here may correspond to step 702 of the method described in FIG. 7B. Such an image 800 may be stored on a computing device 102 where the object edge 804 and the field of view edge 806 can be determined and a rotational angle calculated.

Figure 8B:
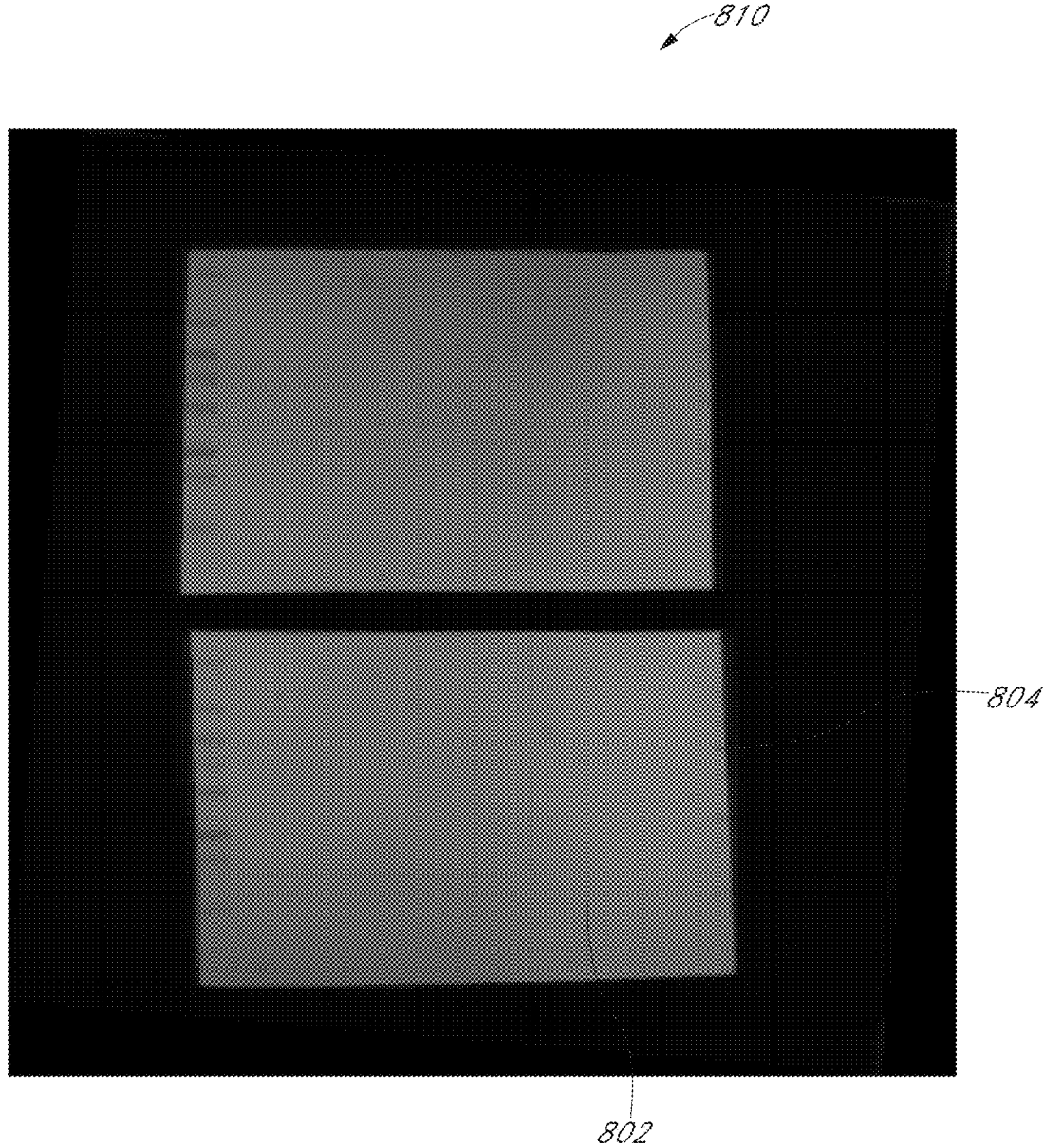
FIG. 8B is an illustration of an electrophoresis gel after a non-optimized field of view has been optimized for rotation according to one of the various embodiments.

Referring to FIG. 8B, a photograph of an object 802 is shown that was rotated by an alignment unit 114 after a computing device 102 analyzed the object edge 804 and field of view edge 806 and instructed the alignment unit 114 according to an embodiment.

Figure 9A:
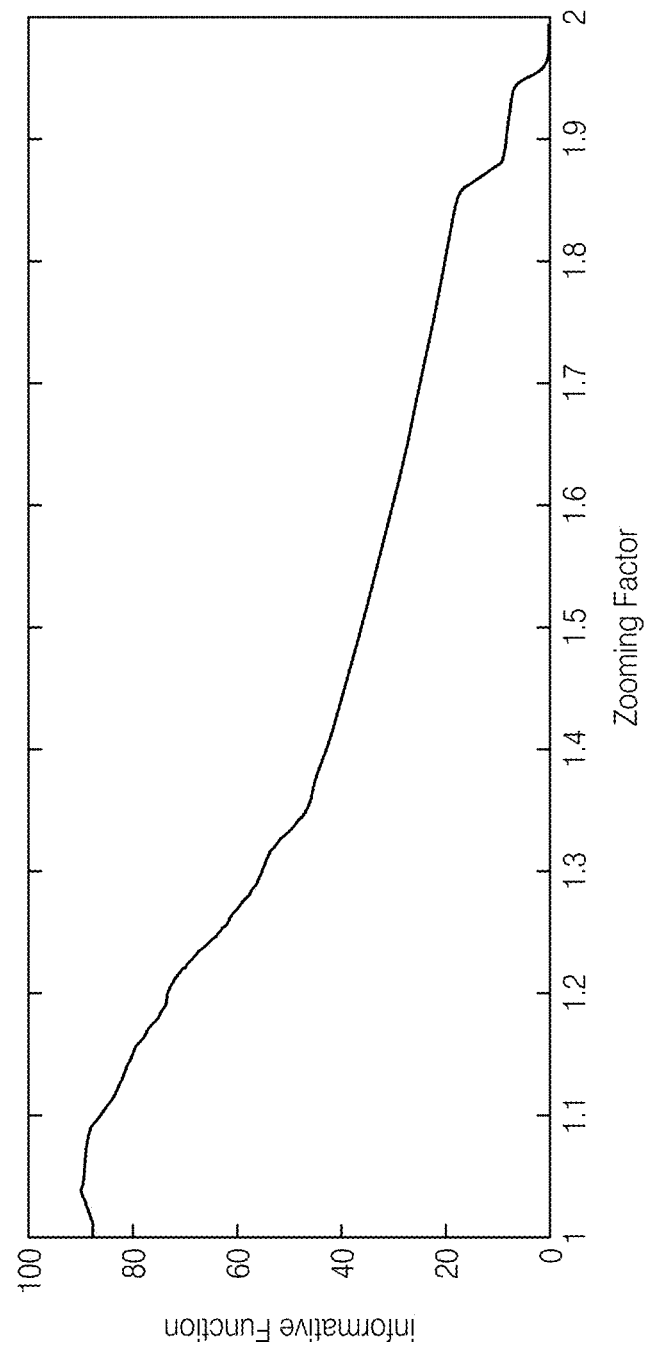
FIG. 9A is an illustration of a graph depicting a zoom factor calculation according to one of the various embodiments.

Referring to FIG. 9A, output of a defined informative function of object 802 at different zoom factors is shown. An informative function can be defined as the sum of high-frequency image signals contained in a field of view divided by the size of the field of view. The zoom factor can produce the highest informative function output which can be selected as the optimal zoom factor. It can define the smallest image region which contains most informative image signals.

Figure 9B:
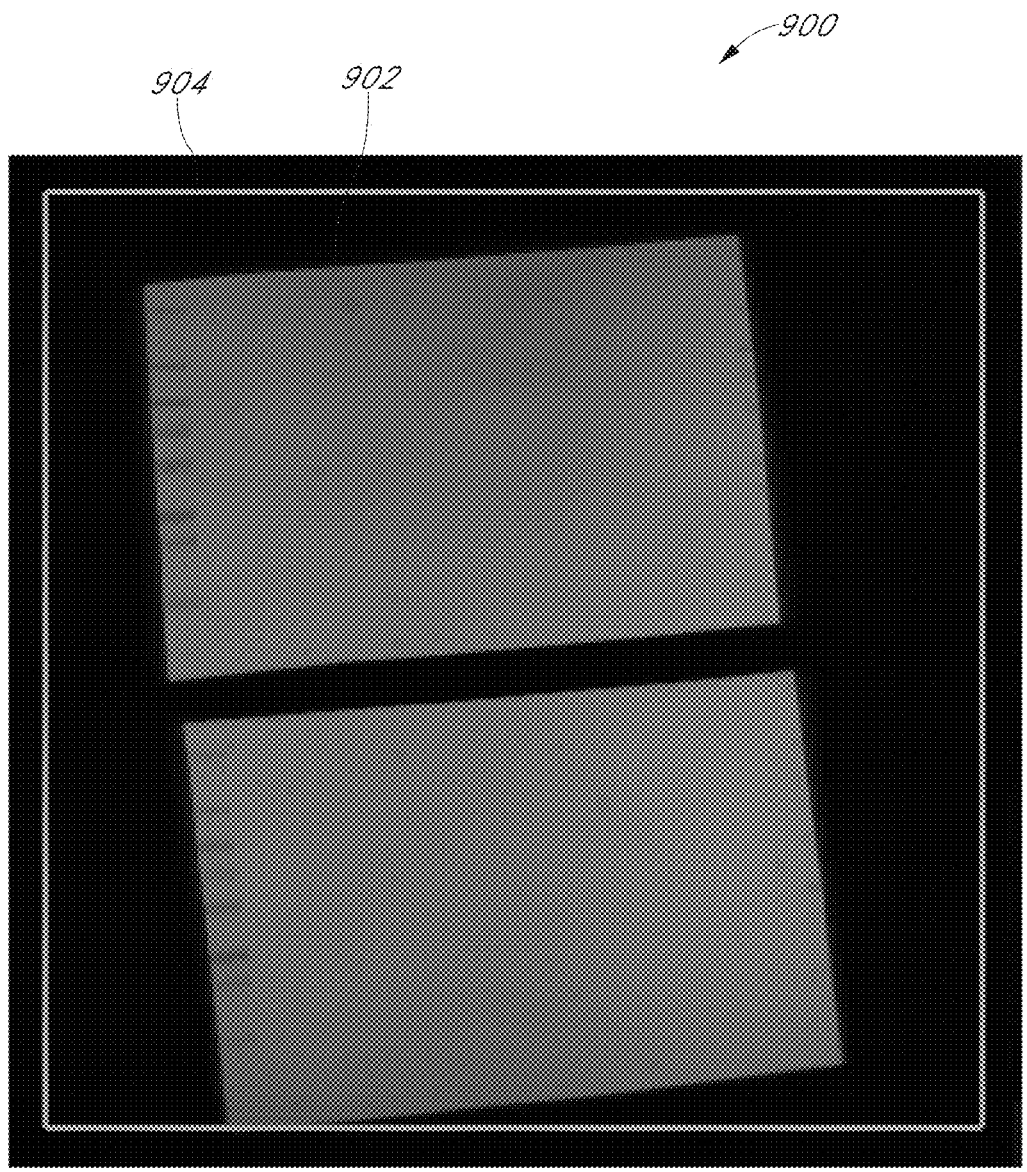
FIG. 9B is an illustration of an electrophoresis gel after a non-optimized field of view has been optimized for zoom according to one of the various embodiments.

Referring to FIG. 9B, a photograph of an object is shown after a zoom factor calculation was completed by the computer device 102 on the object depicted in FIG. 8A. A zoom factor may be calculated by determining where a field of view border 904 is located relative to an object border 902. When any point of the object border 902 is calculated to contact or be adjacent to the field of view border 904 an optimized zoom factor has been determined.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. A system for maximizing a field of view for an image capturing device, the system comprising:
    a surface configured to support an object;
    a camera configured to capture an image of the object in a first position within the field of view;
    a processor including instructions to calculate a rotational angle by virtually aligning an edge of the object with an edge of the field of view and calculating a zoom factor to position the edge of the object along the edge of the field of view.

2. The system of claim 1, wherein the surface is configured to rotate based on the rotational angle and a zoom is adjusted based on the zoom factor.

3. The system of claim 2, wherein the camera is configured to image the object in a second position within the field of view.

4. The system of claim 3, wherein the image from the second position is an optimized image and the optimized image is captured using a larger portion of the field of view than the image of the object in the first position.

5. The system of claim 1, further comprising a display, wherein the processor is configured to create a virtual image based on the calculated rotational angle and present the virtual image on the display.

6. The system of claim 5, wherein the virtual image is configured to be virtually rotated by an end user.

7. The system of claim 6, wherein the camera is configured to image the object in a second position within the field of view.

8. The system of claim 1 further comprising a display, wherein the processor is configured to create a virtual image based on the calculated zoom factor and present the virtual image on the display.

9. The system of claim 8, wherein the virtual image is configured to be virtually zoomed by an end user.

10. The system of claim 9, wherein the object is imaged in a second position within the field of view.

11. A system for maximizing a field of view for an image capturing device, the system comprising:
    an imaging device comprising:
        a rotatable surface configured to hold an object;
        a camera configured to capture an image of the object in a first position within the field of view; and
    a computing device comprising:

a processor including instructions to calculate a rotational angle by virtually aligning an edge of the object with an edge of the field of view and instructions to calculate a zoom factor to position the edge of the object along the edge of the field of view.

12. A method for maximizing a field of view for image capture, the method comprising:
   capturing an image of an object in a first position within the field of view;
   calculating a rotational angle by virtually aligning an edge of the object with an edge of the field of view;
   calculating a zoom factor to position the edge of the object along the edge of the field of view;
   repositioning the object into a second position relative to the field of view based on the rotational angle and the zoom factor; and
   imaging the object in the second position to create a second image.

13. The method of claim 12, wherein the object in the second image covers a larger portion of the field of view than in a first image.

14. The method of claim 12, further comprising a step of creating a virtual representation of a virtually zoomed and rotated image.

15. The method of claim 14, wherein the virtually zoomed and rotated image is configured to be manipulated by an end user.

16. The method of claim 12, wherein the object is an electrophoresis gel.

17. The method of claim 12, wherein the repositioning step uses a moveable surface or a mechanical zoom.

18. A method for increasing a field of view for capturing images, the method comprising:
   capturing an image of an object in a first position within the field of view to generate a first image;
   calculating a rotational angle by virtually aligning an edge of the object with an edge of the field of view;
   rotating the object relative to the field of view based on the calculated rotational angle;
   capturing an image of the object in a second position within the field of view to generate a second image;
   providing machine executable instructions from a memory to a processor to calculate a zoom factor to position the edge of the object along the edge of the field of view;
   increasing a size of the object within the field of view based on the zoom factor; and
   capturing an image of the object in a third position to generate a third image.

19. The method of claim 18 further comprising a step of creating a virtual image, wherein the virtual image can be manipulated by an end user.

20. The method of claim 19, wherein the virtual image is configured to rotate or wherein the virtual image is configured to zoom.

21. The method of claim 18, wherein the object in the third image covers a larger portion of the field of view than in the first image.

22. The method of claim 18, wherein rotating the object comprises rotating a surface holding the object.

23. The method of claim 18, wherein increasing the size of the object within the field of view comprises adjusting a mechanical zoom to achieve the zoom factor.

* * * * *